United States Patent [19]

Venton et al.

[11] 4,239,778
[45] Dec. 16, 1980

[54] AZAPROSTANOIC ACID ANALOGS AND THEIR USE AS INHIBITORS OF PLATELET AGGREGATION

[75] Inventors: Duane L. Venton, Villa Park; Guy C. Le Breton, Chicago, both of Ill.; Steven E. Enke, Lutz, Fla.

[73] Assignee: The University of Illinois Foundation, Urbana, Ill.

[21] Appl. No.: 941,678

[22] Filed: Sep. 12, 1978

[51] Int. Cl.³ .................. C07C 101/04; A61K 31/557
[52] U.S. Cl. .................................. 424/305; 560/121; 562/503; 424/319
[58] Field of Search ........................ 560/121; 562/503; 424/305, 319

[56] References Cited
FOREIGN PATENT DOCUMENTS
2535343 2/1976 Fed. Rep. of Germany ........... 560/121

Primary Examiner—Robert Gerstl
Attorney, Agent, or Firm—Merriam, Marshall & Bicknell

[57] ABSTRACT

Novel azaprostanoic acid analogs of the formula

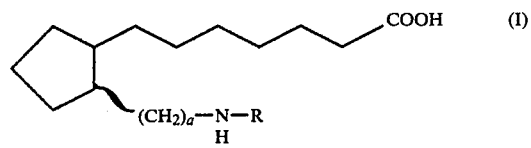

wherein: R is $C_1$ to $C_8$ alkyl or benzyl; and a has a value of from 0 to 6 inclusive, and their pharmaceutically acceptable salts and esters. Preferred 13-aza and 15-aza compounds are active in the inhibition of arachidonic acid-induced platelet aggregation and, more specifically, are direct and specific antagonists of the activity of prostaglandin $H_2$ and thromboxane $A_2$.

9 Claims, No Drawings

AZAPROSTANOIC ACID ANALOGS AND THEIR USE AS INHIBITORS OF PLATELET AGGREGATION

BACKGROUND OF THE INVENTION

The present invention relates to the preparation and use of certain prostanoic acid analogs and more specifically to novel azaprostanoic acids and their use, inter alia, as inhibitors of blood platelet aggregation through selective antagonism of the activity of prostaglandin $H_2$ ($PGH_2$) and thromboxane $A_2$ ($TXA_2$).

In the recent past an enormous amount of research effort has had as its focus the elucidation of the biological properties and activities of blood platelets. In circulation platelets do not normally adhere to each other or to intact blood vessel endothelium but can adhere and spread to non-endothelial surfaces, (e.g., subendothelial collagen at the site of vascular injury) aggregate in response to a variety of stimuli and secrete substances which both cause further aggregation and mediate other biological responses. The so-called "reversible" or "first phase" platelet aggregation may be initiated by the presence of adenosine diphosphate (ADP) and is characterized by clumping of the platelets. "Second phase" or "irreversible" aggregation is marked by platelet synthesis of prostaglandin endoperoxides and $TXA_2$ with subsequent secretion of ADP, serotonin, calcium, and other materials.

Numerous attempts have been made to provide therapeutic agents which would modulate the sequence of biochemical events leading up to platelet aggregation at the site of exposure of subendothelium connective tissue and/or systemically upon the triggering of aggregation processes by substances in the circulatory system. Agents capable of control of the biochemical pathways leading to aggregation would have therapeutic potential in the prevention or treatment of myocardial infarction, myocardial ischemia, pulmonary thromboembolism, disseminated intravascular coagulation, and circulatory complications arising from extracorporeal circulation, oral contraceptive therapy, rheumatic fever, congestive heart failure and the like. See, generally, Weiss, H. J., N.E. Jour. Med., 298 Nos. 24 & 25, pp. 1344–1347, 1403–1406 (1978).

The therapeutic potential of any of the so-called "antiplatelet drugs" must be determined within the context of its specific effects upon the "arachidonic acid cascade" of biochemical reactions leading up to aggregation of platelets during the irreversible phase of aggregation.

Table I below sets forth a simplified schematic representation of the present knowledge of principle biochemical and physiological "events" in the arachidonic acid cascade and metabolism of arachidonic acid within the platelet.

TABLE I

Activating agents

TABLE I-continued

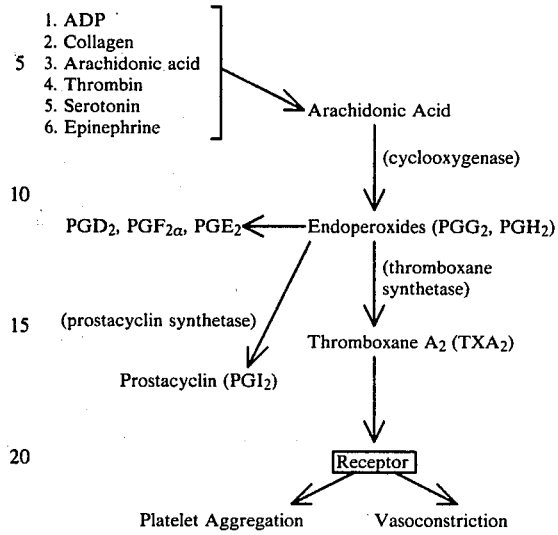

1. ADP
2. Collagen
3. Arachidonic acid
4. Thrombin
5. Serotonin
6. Epinephrine

As noted in Table I, a large number of substances are capable of acting as activating agents in platelet aggregation: ADP; collagen; arachidonic acid; thrombin; serotonin; and epinephrine. Put most simply, arachidonic acid is converted by cyclooxygenase to a series of endoperoxides, $PGG_2$ and $PGH_2$. The endoperoxides are, in turn, subjected to conversion by thromboxane synthetase within the platelet to thromboxane $A_2$. $PGH_2$ and/or $TXA_2$ are believed to operate upon a receptor substance to effect platelet aggregation and vasoconstriction. Essentially simultaneously, endoperoxides can also undergo transformation into the prostaglandins $PGD_2$, $PGE_2$ and $PGF_{2\alpha}$. More significantly, the endoperoxides are precursors for the formation of the potent inhibitor of platelet aggregation, prostacyclin ($PGI_2$). Current evidence leads to the conclusion that during vascular injury platelets sticking to the damaged area "feed" endoperoxides to prostacyclin synthetase in the blood vessel wall adjacent the damaged area, thereby preventing occlusion of the vessel by maintaining a proper balance between a pro-aggregatory agent, $TXA_2$, and an anti-aggregatory agent, $PGI_2$. The presumed mechanism of action of $PGI_2$ resides in its capacity to stimulate an elevation of cyclic adenosine monophosphate (cAMP) levels, while $TXA_2$ is thought to act by depressing cAMP formation.

Although many agents are known to inhibit platelet aggregation in vitro, no effective and benign antithrombotic agent has yet been found. Nonsteroidal anti-inflammatory drugs such as aspirin and indomethacin or the uricosuric agent sulfinpyrazone are known inhibitors of prostaglandin biosynthesis and platelet secretion and have been tested extensively as antithrombotic agents, with controversial results. Aspirin and indomethacin both inhibit prostaglandin biosynthesis by blocking the conversion of substrate fatty acids to endoperoxides by the cyclooxygenase enzyme. Aspirin has been shown to specifically and irreversibly acetylate the active site of the cyclooxygenase. After a single oral dose of aspirin, inhibition of collagen-induced aggregation persists as long as 4 to 7 days, which is the half-life of the platelet.

Aspirin is known to prolong bleeding times and can severely aggrevate the condition of patients with bleeding disorders. However, some success has been reported for the use of aspirin and sulfinpyrazone in the treatment of arterial thrombi, atherosclerosis, and in inhibiting thrombus formation in patients with prosthetic heart valves, as well as in extracorporeal shunts connected to experimental animals. Nevertheless, most aspirin studies have been retrospective with inappropriate controls.

From the point of view of the arachidonic acid cascade in platelets and the possible role of thromboxanes and prostacyclin in hemostasis, the major criticism in the use of aspirin and other non-steroidal anti-inflammatory drugs is their indiscriminant inhibition of this balanced hemostatic control. Thus, by inhibition of the cyclooxygenase enzyme in both platelet and blood vessel wall, the synthesis of both pro-aggregatory ($TXA_2$) and anti-aggregatory ($PGI_2$) agents are blocked. A more rational approach to this problem is acknowledged to be the design of compounds that selectively modulate the various biosynthetic pathways after endoperoxide formation.

Several of the primary prostaglandins, $PGE_1$ and $PGD_2$, appear to be likely candidates as antithrombotic agents. However, their very short biological half-lives preclude their use by oral administration, and must therefore be administered by continuous infusion. Another obvious drawback in the use of primary prostaglandins is their multitude of other physiological activities, primarily stimulation of smooth muscle and gastric secretion, as well as their effects on blood pressure and renal blood flow.

Drugs which selectively inhibit $TXA_2$ formation would be theoretically preferable as antithrombotic drugs since generation of prostacyclin would remain unimpaired. Several compounds are known to selectively inhibit thromboxane synthetase without significantly blocking the cyclooxygenase.

Benzydamine, an anti-inflammatory agent, is more than twice as effective in inhibiting thromboxane synthetase than in inhibiting prostaglandin biosynthesis (cyclooxygenase). Imidazole, selectively inhibits thromboxane synthetase without inducing changes in platelet cAMP levels.

Gorman et al., [P.N.A.S., 74, p. 4007 (1977)] synthesized an azo prostanoic acid analog

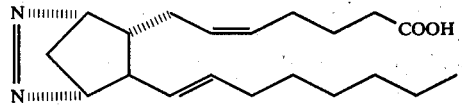

which proved to be a potent inhibitor of thromboxane synthetase, as well as an inhibitor of platelet aggregation induced by $PGH_2$, arachidonic acid, or collagen, and of the second wave of ADP or epinephrine-induced aggregation. Their data also suggest that the azo analog is a competitive inhibitor of $PGH_2$ binding to the thromboxane synthetase enzyme. Inhibition of TX synthetase by the compound led to an increase in $PGE_2$, indicating that the cyclooxygenase enzyme was not affected. In a further study, imidazole and the azo analog have been found to selectively inhibit thromboxane synthetase in a concentration dependent fashion, in both platelet rich plasma and washed platelet suspensions. The azo analog suppressed the attendant aggregation induced by arachidonate in a parallel, concentration-dependent fashion, whereas the influence of imidazole on aggregation was erratic. However, both inhibitors exhibited consistent behavior during aggregation of platelet rich plasma when induced by $PGH_2$. Several important characteristics of these inhibitors could, however, seriously limit their potential use as effective antithrombotic agents. In this respect imidazole appears to also possess direct agonist activity which may explain its ability to potentiate aggregation in washed platelets. In addition, high concentration of imidazole, i.e., 2 mM, are necessary to achieve inhibition of thromboxane synthetase. Furthermore, even though the above-noted azo analog is far more potent in blocking $TXA_2$ synthesis, recent evidence suggests that inhibitory activity may also extend to prostacyclin synthetase. Such an affect could seriously diminish in vivo antithrombotic activity since, as previously mentioned, $PGI_2$ is thought to plate a significant role in reducing platelet reactivity.

While specific inhibition of thromboxane synthetase appears to be a potential route to the development of anti-thrombotic agents, the same effect should be accomplished by selectively antagonizing the action of $TXA_2$ at the receptor level, and this would have the advantage of allowing the entire endoperoxide-thromboxane-prostacyclin system to remain in balance, without the shunting of endoperoxides to unwanted side products. To date, no reports of this approach have appeared in the literature. There exists, therefore, a need in the art for stable, biologically active substances which will selectively antagonize the activity of $TXA_2$ within the arachidonic acid cascade.

BRIEF SUMMARY

The present invention provides certain novel azaprostanoic acid analogs, methods for their synthesis, therapeutic methods for selectively antagonizing the activity of prostaglandin $H_2$ and thromboxane $A_2$, and novel pharmaceutical compositions for administration to patients in need of blood platelet anti-aggregatory therapy.

The following structure is ascribed to prostanoic acid.

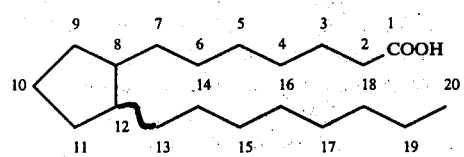

By convention, the carbon atoms of the structure are numbered sequentially from the carboxylic carbon atom.

The compounds provided according to the invention comprise azaprostanoic acid analogs of the formula I,

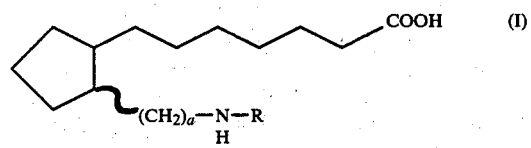

wherein: R is $C_1$ to $C_8$ alkyl or benzyl; and a has a value of from 0 to 6 inclusive and their pharmaceutically acceptable salts and lower alkyl esters.

Preferred compounds of formula I include the 13-azaprostanoic acid analogs (wherein a has a value of 0 and the nitrogen atom occupies the position of the "13" carbon atom), to wit, compounds of the formula II,

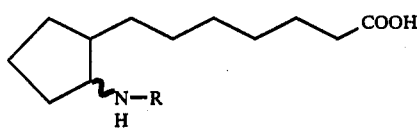 (II)

and the 15-azaprostanoic acid analogs (wherein a has a value of 2), to wit, compounds of the formula III,

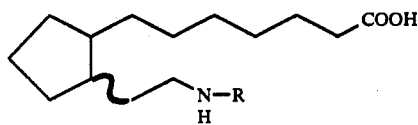 (III)

The synthetic method of the invention for preparation of 13-aza compounds of formula II proceeds by way of condensation of the lower alkyl (i.e., $C_1$ to $C_3$) keto ester 1b (prepared from the keto acid, 1a) with a variety of amines of the general formula $RNH_2$ (wherein R has the value set out above), reduction of the Schiff base so formed, and hydrolysis to the free acid, as indicated below.

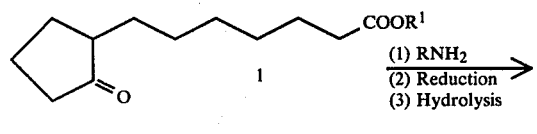

1a, $R^1$ = H
1b, $R^1$ = $C_1$ to $C_3$ alkyl

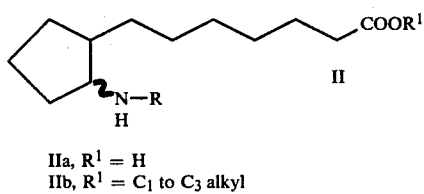

IIa, $R^1$ = H
IIb, $R^1$ = $C_1$ to $C_3$ alkyl

The keto ester reactant, 1b, is suitably prepared in acceptable yields by the base catalyzed alkylation of the salt of a selected carboalkoxycyclopentanone (e.g., potassium salt of 2-carboethoxycyclopentanone) with a suitable haloheptanoic acid (e.g., 7-bromoheptanoic acid) to give the diester, 2, which is transformed by hydrolysis and decarboxylation to the final product, as indicated below.

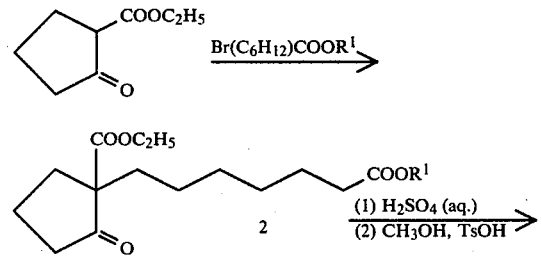

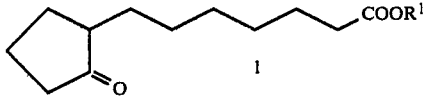

While the above direct amination procedure for preparation of azaprostanoic acids may be employed in the synthesis of compounds wherein the nitrogen is in the "13" position, it cannot be employed successfully to prepare the "14" or higher-numbered position analogs. Preparation of azaprostanoic acid analogs wherein it is desired to have the nitrogen atom in the "14" or higher-numbered position may be effected by the amination process first noted, but carried out on a selected aldehyde derivative, 3, of the cyclopentanone.

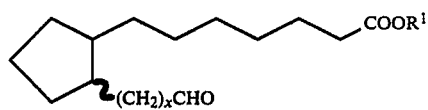 3 wherein: x has a value of 0 to 5 inclusive. The aldehyde, 3, is prepared by one or more Wittig transformations according to the method of Kurozumi, et al., Kokai, 75 05 364; Chem. Abstracts, 82, 155541µ (1975). A procedure for synthesis of the 14-aza analogs is illustrated below.

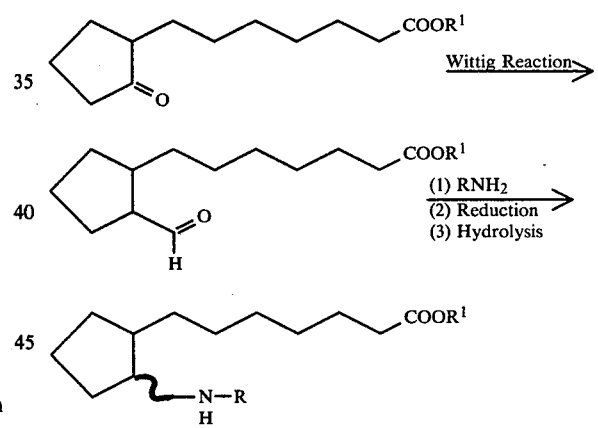

Preparation of the 15-aza compounds of formula III, may also be effected by reaction of the keto ester, 1b, with the lithium salt of a selected alkoxyiminovinyl phosphonate of the formula

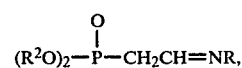

wherein $R^2$ is lower alkyl. This is followed by catalytic reduction as set forth in the following illustrative scheme wherein the 15-aza compound is formed through use of diethoxyiminovinyl phosphonate.

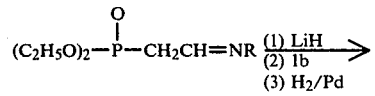

-continued

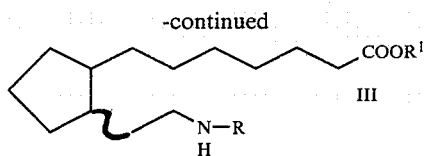

IIIa, R = H
IIIb, R = C₁ to C₃ alkyl

The above-noted reaction of the imminovinyl phosphonate may also be performed on any desired aldehyde derivative, 3, described above.

Compounds of the invention are shelf stable over long periods of time in either their ester or free acid forms.

The therapeutic methods of the present invention provide for selectively antagonizing the activity of PGH$_2$ and TXA$_2$ within the arachidonic acid cascade by administration of effective amounts of the compounds of the invention to an animal in need of antiplatelet, e.g., antithrombotic, therapy.

The pharmaceutical compositions of the invention, useful within the context of antiplatelet therapy, comprise effective amounts (1 to 100 mg/kg doses) of the azaprostanoic acids of the invention and/or their salts and esters in combination with pharmaceutically acceptable diluents, carriers, and/or excipients.

Numerous aspects and advantages of the present invention will become apparent upon consideration of the following detailed description of preferred embodiments.

DETAILED DESCRIPTION

The following examples illustrate preparation of 13-azaprostanoic acid analogs of the formula II

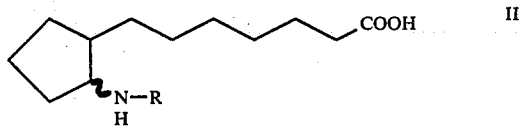

wherein: R is C$_1$ to C$_8$ alkyl or benzyl.

More specifically the examples illustrate preparation of: cis-2-(N-benzylamino)-1-(6-carbomethoxyhexyl)cyclopentane and its trans isomer; cis-2-(N-benzylamino)-1-(6-carboxyhexyl) cyclopentane and its trans isomer; cis-13-azaprostanoic acid and its trans isomer; cis-13-aza-20-norprostanoic acid and its trans isomer; cis-13-aza-20-homoprostanoic acid and its trans isomer.

In the following examples all melting points were determined in capillary tubes on a Thomas Hoover melting point apparatus and are uncorrected. Proton magnetic resonance (Pmr) spectra were recorded by means of a Varian T-60A spectrometer equipped with a Nicolet TT-7 Fourier Transform accessory. Chemical shifts are reported in ppm downfield from internal (CH$_3$)$_4$Si. Mass spectra were obtained at 70 eV using a Hitachi Perkin-Elmer RMU-6D single focusing mass spectrometer. Infrared (IR) spectra were obtained on a Perkin-Elmer 337 recording infrared spectrophotometer. Thin layer chromatographs (tlc) were developed on 10 cm slides coated with silica gel and a fluorescent indicator (Eastman Chromagram Sheet 6060). Spots were visualized by ultraviolet light, iodine vapor, or nitro-prusside-acetaldehyde spray reagent, where appropriate. Reaction mixtures were routinely analyzed by gas-liquid chromatography using a Hewlett Packard 5750 Research Cromatograph fitted with a 10', 3% SE-30 analytical column (⅛ in. OD). Preparative gas chromatography employed a 20', 30% SE-30 preparative column (⅜ in. O.D.).

EXAMPLE 1

2-(6-Carbomethoxyhexyl)cyclopentanone

The above-named compound, which is employed in each of the following preparations of compounds of the invention is prepared as follows.

To 3.30 g (15.6 mmole) of 2-(6-carboxyhexyl)cyclopentanone [prepared according to the method of Novak, et al., Synthesis, p. 353 (1974)] in anhydrous methanol (60 ml) is added 0.25 g p-toluenesulphonic acid, and the mixture is stirred overnight at 25° C. The excess methanol is evaporated, the residue dissolved in ether, and the solution washed one time with ice-cold 5% aqueous NaHCO$_3$, on time with water, dried over anhydrous K$_2$CO$_3$, filtered, and concentrated to give 3.27 g (14.5 mmole, 93%) of the desired product. An analytical sample is obtained by preparative GLC; pmr (CCl$_4$) δ3.67 (s, 3H, CO$_2$CH$_3$), 2.6–1.0 (complex m, 19H); mass spectrum (70 eV) m/e (rel intensity) 226 (6), 195 (8), 194 (5), 143 (6), 111 (8), 97 (9), 84 (100), 83 (17). Analysis calculated for C$_{13}$C$_{22}$O$_3$: C, 68.99; H, 9.78. Found: C, 68.97; H, 9.78.

EXAMPLE 2 cis-2-(N-Benzylamino)-1-(6-carbomethoxyhexyl)cyclopentane and its trans isomer

To a solution of 2-(6-carbomethoxyhexyl)cyclopentanone of Example 1 (2.52 g, 11 mmole) in 45 ml absolute methanol and containing 3 g 3A molecular sieves is added, dropwise, 2.40 g (22 mmole) benzylamine. The mixture is stirred at room temperature for 16 hours. After cooling in an ice-bath, 98% sodium borohydride (0.43 g, 11 mmole) is added and the reaction mixture stirred for 20 minutes. The excess borohydride is decomposed by the addition of 1 ml acetone. The resulting solution is poured into water, saturated with NaCl and extracted with ether. Combined extracts are concentrated in vacuo, the residue dissolved in hexane and dried over sodium sulfate, filtered and concentrated to give 2.99 g of a colorless oil. Column chromatography of 230 mg of the oil on 80 g silica gel with ether-hexane 1:1 gives the cis isomeric product (56 mg, 21%). R$_f$ value (silica, Eastman 6060): ether, 0.57; pmr (CCl$_4$) δ7.26 (s, 5H, aromatic), 3.73 (d, J$_{AB}$=13 Hz, 2H, benzylic methylene), 3.63 (s, 3H, CO$_2$CH$_3$), 3.20–2.85 (m, 1H, CHN), 1.05 (broad resonance, 1H, NH, D$_2$O exchangeable); mass spectrum (70 eV) m/e (rel intensity) 317 (15), 316 (8), 226 (13), 202 (8), 188 (8), 146 (70), 108 (33), 106 (27), 91 (100). Analysis calculated for C$_{20}$H$_{31}$NO$_2$: C, 75.66; H, 9.84. Found: C, 75.95; H, 9.82.

Further elution of the column prepared for the above cis-isomer with ether-hexane 1:1 gives the corresponding trans-isomer (122.5 mg, 46%). R$_f$ value (silica, Eastman 6060): ether, 0.44, pmr (CCl$_4$) δ7.23 (s, 5H, aromatic), 3.75 (d, J$_{AB}$=13 Hz 2H, benzylic methylene), 3.63 (s, 3H, CO$_2$CH$_3$), 2.85–2.45 (m, 1H, CHN), 1.10 (broad resonance, 1H, NH, D$_2$O exchangeable). Analysis calculated for C$_{20}$H$_{31}$NO$_2$: C, 75.66; H, 9.84. Found: C, 75.50; H, 10.02.

EXAMPLE 3 cis-2-(N-Benzylamino)-1-(6-carboxyhexyl)cyclopentane and its trans isomer

The cis-benzylamino ester of Example 2 (912 mg, 2.9 mmole) is boiled (about 4 hours) with stirring in 15 ml 2.5% aqueous sodium hydroxide until a homogeneous solution is obtained. After cooling, the solution is acidified by dropwise addition of 5% aqueous hydrochloric acid, then made strongly basic by addition of excess concentrated ammonium hydroxide, and heated gently to expel excess ammonia. The crude amino acid is collected by filtration, washed with water, and air dried to give the desired cis-N-benzylamino derivative (701 mg, 80%) as a white, microcrystalline powder, having a melting point 126°–128° C. Four recrystallizations from ethanol-water gives the analytical sample: melting point 129°–130° C., mass spectrum (70 eV m/e (rel intensity) 303 (9), 146 (87), 91 (100). Analysis calculated for $C_{19}H_{29}NO_2$: C, 75.21; H, 91.63; N, 4.62. Found: C, 75.34; H, 9.59; N, 4.57.

The trans-benzylamino ester of Example 2 (736 mg, 2.3 mmole) is hydrolyzed in the same manner as the cis-isomer to give the white crystalline trans-N-benzylamino derivative (626 mg, 89%), melting point 148.5°–150° C. Two recrystallizations from ethanol give the analytical sample: melting point 151°–151.5° C.; mass spectrum (70 eV) m/e (rel intensity) 303 (8), 146 (75), 91 (100). Analysis calculated for $C_{19}H_{29}NO_2$: C. 75.21; H, 9.63; N, 4.62. Found: C, 75.04; H, 9.63; N, 4.33

EXAMPLE 4 cis-13-Azaprostanoic acid and its trans isomer

To a solution of 2-(6-carbomethoxyhexyl)cyclopentanone of Example 1 (2.0 g, 8.8 mmole) in 45 ml absolute methanol is added dropwise n-heptylamine (2.04 g, 17.7 mmole). The solution is stirred in a nitrogen atmosphere at room temperature for 44 hours. After cooling in an ice-bath, 98% sodium borohydride (0.36 g, 9.3 mmole) is added and the mixture stirred for 30 minutes. The excess borohydride is decomposed by the addition of 1 ml acetone. The solvents are removed in vacuo and the residue taken up in ether, washed twice with saturated sodium chloride and once with water, dried over potassium carbonate, filtered, and concentrated to give 3.23 g yellow oil. Column chromatography of this oil on 75 g silica gel with ether-hexane (62.5:37.5) gives the cis-13-azaprostanoic acid methyl ester (790 mg, 28%). $R_f$ value (silica, Eastman 6060): ether, 0.61; pmr ($CCl_4$) δ3.60 (s, 3H, $CO_2CH_3$), 3.20–2.80 (m, 1H, CHN). The ester (790 mg, 2.4 mmole) is hydrolyzed by the procedure of Example 3 to give the amino acid (498 mg, 66%), having a melting point of 98.5°–103.5° C. Three recrystallizations from ethanol-water gives the analytical sample: melting point 107.5°–108.5° C.; mass spectrum (70 eV) m/e (rel intensity) 311 (10), 226 (100), 154 (64). Analysis calculated for $C_{19}H_{37}NO_2$: C, 73.26; H, 11.97; N, 4.50. Found: C, 73.41; H, 11.99; N, 4.40.

Further elution of the column prepared for the methyl ester of the cis-isomer with ether-hexane (62.5:37.5) gives the trans-13-azaprostanoic acid methyl ester (901 mg, 32%). $R_f$ value (silica, Eastman 6060): ether, 0.49; pmr ($CCl_4$) δ3.60 (s, 3H, $CO_2CH_3$), 2.80–2.45 (m, 1H, CHN). Hydrolysis and work up of the trans-methyl ester (901 mg, 2.8 mmole) gives the amino acid (547 mg, 63%), having a melting point of 112°–114.5° C. Two recrystallizations from ethanol-water gives the analytical sample: melting point 115.5°–116° C.; mass spectrum (70 eV) m/e (rel intensity) 311 (10), 226 (100), 154 (67). Analysis calculated for $C_{19}H_{37}NO_2$: C, 75.26; H, 11.97; N, 4.50. Found: C, 73.19; H, 11.86; N, 4.42.

EXAMPLE 5 cis-13-Aza-20-norprostanoic acid and its trans isomer

Following the procedure used for the synthesis of the azaprostanoic acids of Example 4, 2-(6-carbomethoxyhexyl)cyclopentanone (1.6 g, 7 mmole) and n-hexylamine (1.4 g, 14 mmole) gives 2.68 g of yellow oil after borohydride reduction and work-up. Column chromatography of 2.48 g of the oil on 80 g silica gel with ether-hexane 3:1 gives cis-13-aza-20-norprostanoic acid methyl ester (0.72 g, 35%). $R_f$ value (silica, Eastman 6060): ether, 0.55; pmr ($CCl_4$) δ3.63 (s, 3H, $CO_2CH_3$), 3.10–2.75 (m, 1H, CHN). The ester (0.72 g, 2.3 mmole) is hydrolyzed and worked up to give the cis-amino acid (0.28 g, 41%). Four recrystallizations from ethanol-water gave the analytical sample: melting point 86.5°–87.5° C.; mass spectrum (70 eV) m/e (rel intensity) 297 (8), 226 (100), 140 (88). Analysis calculated for $C_{18}H_{35}NO_2$: C, 72.68; H, 11.86; N, 4.71. Found: C, 72.60; H, 11.71; N, 4.52.

Further elution of the column prepared for the methyl ester of the cis-isomer with ether-hexane 3:1 gives trans-13-aza-20-norprostanoic acid methyl ester (0.64 g, 31%). $R_f$ value (silica, Eastman 6060): ether, 0.46; pmr ($CCl_4$) δ3.63 (s, 3H, $CO_2CH_3$), 2.75–2.49 (m, 1H, CHN). The ester (0.64 g, 2.1 mmole) was hydrolyzed and worked up to give the trans-amino acid (0.43 g, 70%), having a melting point 112°–114° C. Three recrystallizations from ethanol-water gives the analytical sample: melting point 115°–115.5° C.; mass spectrum (70 eV) m/e (rel intensity) 297 (9), 226 (100), 140 (87). Analysis calculated for $C_{18}H_{35}NO_2$: C, 72.68; H, 11.86; N, 4.71. Found: C, 72.65; H, 12.02; N, 4.68.

EXAMPLE 6 cis-13-Aza-20-homoprostanoic acid and its trans isomer

Following the procedure used for the synthesis of the azaprostanoic acids of Example 4, 2-(6-carbomethoxyhexyl)cyclopentanone (1.6 g, 7 mmole) and n-octylamine (1.8 g, 14 mmole) gives 3.13 g of yellow oil after borohydride reduction and work-up. Column chromatography of the oil on 75 g silica gel with ether-hexane (62.5/37.5) gives cis-13-aza-20-homoprostanoic acid methyl ester (0.84 g, 35%). $R_f$ value (silica, Eastman 6060): ether, 0.52; pmr ($CCl_4$) δ3.61 (s, 3H, $CO_2CH_3$), 3.10–2.70 (m, 1H, CHN). The ester (0.84 g, 2.5 mmole) is hydrolyzed and worked up to give the cis-amino acid (0.78 g, 97%). Two recrystallizations from ethanol-water gives the analytical sample: melting point 8.65°–87.5° C.; mass spectrum (70 eV) m/e (rel intensity) 325 (10), 226 (100), 168 (56). Analysis calculated for $C_{20}H_{39}NO_2$: C, 73.79; H, 12.08; N, 4.30. Found: C, 73.86; H, 12.10; N, 4.02.

Further elution of the column prepared for the methyl ester of the cis-isomer with ether-hexane (62.5/37.5) gives trans-13-aza-20-homoprostanoic acid methyl ester (0.67 g, 28%). $R_f$ value (silica, Eastman 6060): ether, 0.40; pmr ($CCl_4$) δ3.61 (s, 3H, $CO_2CH_3$), 2.75–2.45 (m, 1H, CHN). The ester (0.67 g, 2.0 mmole) was hydrolyzed and worked up to give the trans-amino acid (0.53 g, 83%). Four recrystallizations from ethanol-water gives the analytical sample: melting point 110.5°–111.5° C.; mass spectrum (70 eV) m/e (rel intensity) 325 (10), 226 (100), 168 (61). Analysis calculated for $C_{20}H_{39}NO_2$: C, 73.79; H, 12.08; N, 4.30. Found: C, 73.80; H, 11.86; N, 4.08.

The following example illustrates preparation of azaprostanoic acid analogs of the invention and reactants for its synthesis.

EXAMPLE 7

Diethyl 2-(n-pentylimino)ethylphosphonate

To a solution of diethylformylmethylphosphonate (8.1 g, 45 mmole) in 50 ml absolute methanol at ice-bath temperature in a nitrogen atmosphere is added, dropwise, n-pentylamine (3.0 g, 45 mmole). The mixture is stirred at room temperature for 20 minutes. After removal of the solvent in vacuo, the residue is dissolved in ether, dried over potassium carbonate, filtered and concentrated to give 9.5 g of a yellow oil. Short-path distillation out of potassium carbonate (about 200 mg) gives the desired phosphonate (6.0 g, 54%): ir (neat) 3270 (broad, NH), 1620 cm$^{-1}$ (—CH$_2$CH=N—$\rightleftarrows$—CH=CHNH—); pmr (CCl$_4$) 7.40–6.20 (m, 2H, —CH=CH—), 4.30–3.60 (m, 4H, —CCH$_2$CH$_3$), 1.25 (t, J=7 Hz, —OCH$_2$CH$_3$); mass spectrum (70 eV) m/e (rel. intensity) 249 (31), 220 (24), 206 (23), 192 (100), 165 (23), 164 (30), 152 (14), 136 (37), 118 (23), 112 (27), 111 (25), 98 (35). Analysis calculated for $C_{11}H_{29}NO_3P$: C, 53.00; H, 9.70. Found: C, 52.95; H, 9.52.

EXAMPLE 8

15-Azaprostanoic acid

To lithium hydride (0.124 g, 15 mmole) in 3 ml tetrahydrofuran (THF) is added dropwise a solution of the phosphonate of Example 7 (3.81 g, 15 mmole) in 14 ml THF. The solution is gently heated (70°–80° C.) with stirring in a nitrogen atmosphere overnight. After cooling, a solution of keto-ester of Example 1 (1.54 g, 6.8 mmole) in 8 ml THF is added and stirred at room temperature under nitrogen for 9 hours. The mixture is poured onto crushed ice and extracted with ether. The combined extracts are dried, filtered, and concentrated to give 4.67 g of a yellow oil. The oil is dissolved in 200 ml 95% ethanol to which is added 200 mg 5% pladadium on charcoal, and the solution shaken for 3.5 hours at 40 psi hydrogen pressure. Filtration and concentration gave 4.17 g yellow oil. To this oil is added 60 ml 2.5% aqueous sodium hydroxide and the mixture boiled with stirring until a homogeneous solution is obtained (2 hours). After cooling, 5% hydrochloric acid is added dropwise until acidic, then concentrated ammonium hydroxide added until strongly basic. The mixture is heated gently with stirring to expel excess ammonia and a dark orange oil separates out of solution. The solution is extracted several times with octanol and the combined extracts concentrated in vacuo with gentle heating (40°–70° C.) to give 3.75 g dark yellow oil. Column chromatography of 0.99 g of the oil on 70 g silica gel and elution with CHCl$_3$—MeOH—NH$_4$OH 94:5:1 gives 203.2 mg of the major isomer of the desired compound. Three recrystallizations from ethanol-water gives the analytical sample: melting point 107°–107.5° C.; mass spectrum (70 eV) m/e (rel intensity) 311 (6), 254 (30), 100 (100). Analysis calculated for $C_{19}H_{37}NO_2$: C, 73.26; H, 11.97; N, 4.50. Found: C, 73.28; H, 11.95; N, 4.46.

Further elution of the above column gives 19.9 mg of the minor isomer of the desired compound. The mass spectrum of this product is essentially identical to the spectrum obtained for the major isomer.

In the foregoing preparations illustrated by Examples 2 through 6, compounds of the general formula I were prepared whrein a has a value of 0, and R is illustrated by benzyl, n-hexyl, n-heptyl, and n-octyl groups. It will be understood that compounds of formula I wherein R represents a $C_1$ through $C_5$ group may be easily prepared through use of the appropriate alkyl amine. In a like manner, in the illustrative preparation of Example 8, a compound of the general formula I is prepared wherein a has a value of 2 and R is represented by an n-pentyl group. Preparation of compounds wherein a has a value of 1 or more are prepared through use of the aldehyde intermediate and either the amine or iminovinyl phosphonate as noted previously.

As will be apparent from the following examples treating the pharmacological activity of compounds of the invention, the presently preferred compounds of the invention are those comprehended by formula I in which the numerical sum of the amine and methylene plus the terminal methyl groups approximates the total of methylene groups plus the terminal methyl group in prostanoic acid, i.e., 8. Thus, where a has a value of 0 in a compound of formula I, R is preferably $C_7$ alkyl. Likewise, where a has a value of 2, R is preferably a $C_5$ alkyl group.

The above examples 2 through 6 and 8 are also seen to illustrate preparation of the free acid compounds and their methyl esters. It will be understood by those skilled in the art that homologous, lower alkyl ($C_1$ to $C_3$) esters and pharmaceutically acceptable salts of the free acids may be prepared without departing from the spirit of the invention.

A representative sample of the 13-azaprostanoic acid derivatives, and cis-15-azaprostanoic acid were tested for their effect as inhibitors of prostaglandin synthetase (cyclooxygenase). The basis of the assay is the measurement of the arachidonic acid-dependent formation of adrenochrome from L-peinephrine during prostaglandin biosynthesis [See, generally, the procedure of Takaguchi, et al., Prostaglandins, 2, 169 (1972)]. The cis- and trans-13-azaprostanoic acids of Example 4, the trans-13-aza-20-norprostanoic acid analog of Example 5 and the trans-benzyl derivative of Example 3 did not significantly inhibit the cyclooxygenase at a concentration of $5\times10^{-4}$ M. Likewise, cis-15-azaprostanoic acid, failed to inhibit the enzyme at $1\times10^{-4}$ M. Weak inhibitory activity on the order of 30% was observed with the cis- and trans-13-aza-20-homo analogs of Example 6. Under these assay conditions, 100% inhibition of enzyme activity was produced by indomethacin at $2\times10^{-5}$ M.

The effect of various azaprostanoic acids of the invention on arachidonic acid-induced platelet aggregation was determined according to the method of Born, Nature, 194, 927 (1962). At a concentration of 10 μM, trans-13-azaprostanoic acid, and cis-15-azaprostanoic acid, inhibit aggregation 100% and 91%, respectively in response to 300 μM arachidonare. Both the cis and trans-13-aza-20-homoprostanoic acid analogs show significant inhibitory activity, 50% and 71%, respectively. At this concentration, the cis-13-aza and trans-13-aza-N-benzyl derivative is inactive.

No effect was observed on the ADP-induced primary aggregation of platelets. Thus, pretreatment (2 min.) of human platelet rich plasma (PRP) with 100 μM of cisor trans-13-azaprostanoic acid, trans-13-aza-N-benzyl derivative or cis-15-azaprostanoic acid, followed by injection of 10 μM ADP did not alter reversible, primary phase aggregation relative to control with ADP alone.

The relative inhibitory activities of the azaprostanoic acids were determined by varying the concentration of arachidonic acid while keeping the inhibitor concentration constant. These data are summarized in Table II, below.

TABLE II

Inhibition of Arachidonic Acid-induced Platelet Aggregation (Human PRP) by Azaprostanoic acids at $10^{-5}$ M Concentrations

| Example No. | Stereo-chemistry | % Inhibition conc. (μM) arachidonate | | |
|---|---|---|---|---|
| | | 500 | 400 | 300 |
| 4 | trans | 19 | 66 | 100 |
| 4 | cis | 0 | 11 | 43 |
| 6 | trans | 0 | 7 | 71 |
| 6 | cis | 0 | 11 | 50 |
| 5 | trans | 0 | 0 | 14 |
| 3 | trans | 0 | 0 | 0 |
| 8 | cis | 0 | 16 | 91 |

The effect of trans-13-azaprostanoic acid on platelet aggregation induced by externally generated endoperoxides and thromboxane A$_2$ was investigated. The endoperoxides and thromboxane A$_2$ were generated by the addition of 500 μM arachidonic acid to 0.75 ml of human platelet-rich plasma (PRP). After 40 seconds, 200 μl of this solution was transferred to a second cuvette of human PRP pretreated with aspirin (0.5 mg/ml). The endoperoxides and thromboxane transferred caused the aspirin-treated platelets to aggregate. This aggregation is not due to transferred arachidonic acid, since treatment of the aspirin-treated platelet suspension with 500 μM arachidonic acid did not cause aggregation. On the other hand, when the aspirin-treated platelets are pre-incubated with 100 μM trans-13-azaprostanoic acid, no aggregation was observed when the endoperoxide/thromboxane mixture was added.

The following example illustrates in vivo antithrombotic activity of compounds of the invention.

EXAMPLE 9

Swiss Webster mice (25 gm) maintained on a Purina diet were injected intraperitoneally with either 0.1 ml corn oil or 0.1 ml corn oil containing 13-azaprostanoic acid (13-APA) of Example 5. The dose of 13-APA employed was 30 mg/kg. One hour subsequent to injection, 0.05 ml of a sodium arachidonate solution was administered by rapid I.V. through the tail vein to both control and drug-treated mice. The arachidonate was dissolved in 90% saline and 10% ethanol (95%). Appropriate controls were performed to insure that the ethanol itself did not produce undesirable effects.

The results set out in Table III indicate that in the untreated mice, I.V. arachidonate (100 mg/kg) produces immediate and severe respiratory distress which resulted in one death within 30 seconds. On the other hand, the mice which were pretreated with 13-APA underwent none of the symptoms of thromboembolism associated with arachidonate (100 mg/kg) injection.

TABLE III

| | Severe Respiratory Distress | Death |
|---|---|---|
| Control (4) | 4 | 1 |
| 13-APA (4) | 0 | 0 |

The present preliminary findings when considered in combination with the in vitro studies noted previously indicate that 13-APA is an effective antithrombotic agent in vivo, that it effectively crosses biological membranes, and that the compound is not rapidly degraded in vivo. While the toxicity of 13-APA remains to be fully evaluated, months after a dose of 30 mg/kg no ill effects are evident in the test animals. This suggests that acute administration of 13-APA is not highly toxic.

It is expected that unit doses of from 1 mg/kg to about 100 mg/kg of compounds the invention will, when administered orally or parenterally and in combination with pharmaceutically acceptable carriers, diluents and excipients, provide desired antiplatelet (e.g., antithrombotic) therapeutic effects.

Biological screening of the azaprostanoic acids of the invention has revealed that several of the derivatives, most notably trans-13-azaprostanoic acid, are potent inhibitors of platelet aggregation. As might be expected by the similarity of these compounds to the prostaglandins, their inhibitory activity is specific to the platelet arachidonic acid cascade. This is born out by the observation that none of the derivatives tested had inhibitory activity on the primary, reversible phase of ADP-induced aggregation. In addition, this indicates that the azaprostanoic acids do not act on the platelet by a non-specific effect, such as deformation of the platelet membrane.

The inhibitory effect of the 13-azaprostanoic acids on arachidonate-induced platelet aggregation is apparently sensitive not only to stereochemical configuration but also to the length of the amino side chain. Thus, all of the cis isomers and the 20-nor and 20-homo analogs, regardless of stereochemistry, show decreased activity when compared with the aza analog of the natural prostaglandin skeletal arrangement. The generally reduced inhibitory activity of the structurally altered prostanoic acid analogs is surprising in view of other structure-activity relationships which have revealed that although 20-nor-PGE$_1$ is only half as potent as PGE$_1$ as an inhibitor of ADP-induced aggregation, the corresponding 20-homo-PGE$_1$ is 3.82 times more potent that PGE$_1$. Likewise, the 8,12-cis analog of PGE$_1$ is reported to be equipotent to PGE$_1$ as an inhibitor of ADP-induced aggregation. Thus, the inhibitory activity of the azaprostanoic acids display an unusual degree of stereospecificity, and coupled with their potency, indicates that their site of action occurs at a receptor level.

Preliminary experiments on the platelet lead to postulation that these compounds might be acting at one of three distinctly different sites. First, the inventive compounds might be inhibitors of the cyclooxygenase enzyme complex which transforms the fatty acid precursors to the prostaglandin endoperoxides PGG$_2$ and PGH$_2$. In this regard, they would have a similar mode of action as do the non-steroidal anti-inflammatory agents such as aspirin and indomethacin. A second potential site of action might be the inhibition of thromboxane synthetase, thereby blocking the transformation of the endoperoxides to the pro-aggregatory agent thromboxane A$_2$, similar to the actions of imidazole and above-noted azoendoperoxide analog. The third possible site of action could be the inhibition of thromboxane A$_2$ and/or the endoperoxides at their receptor site(s). To date, no inhibitors have been reported that act by this last-mentioned mechanism.

In order to check the possibility that the compounds might be inhibitors of the cyclooxygenase enzyme, they were tested in a standard prostaglandin biosynthesis assay according to the method of Takagushi, et al., Prostaglandins, 2, 169 (1972). The basis of the assay is the measurement of the arachidonic acid-dependent formation of adrenochrome from L-epinephrine during prostaglandin biosynthesis. Although the assay is an indirect measurement of cyclooxygenase activity, it offers the advantage that total enzyme activity is measured and is not limited to the measurement of any one product of the biotransformation. The azaprostanoic acids, when tested by this assay method, were found to have very little or no effect on prostaglandin synthetase (cyclooxygenase) derived from bovine seminal vesicles. The most potent inhibitor on the platelet, trans-13-azaprostanoic acid, had less than 10% inhibitory activity on the cyclooxygenase at a concentration 2 orders of magnitude greater than that necessary for 100% inhibition of platelet aggregation. At the high concentration tested in this assay system ($5 \times 10^{-4}$ M), only the cis and trans-20-homo analogs showed significant inhibitory activity (approximately 30%). These findings are consistent with the above-noted observations on the increased inhibitory activity of 20-homo-prostaglandins. Under identical assay conditions, prostaglandin biosynthesis was completely inhibited by indomethacin at a concentration of $2 \times 10^{-5}$ M.

It can be concluded, therefore, that the inhibitory activity of the azaprostanoic acids on platelet aggregation is not caused by inhibition of the platelet cyclooxygenase enzyme system. Although the assay employed a cyclooxygenase preparation derived from bovine seminal vesicles, there is considerable evidence to suggest that the enzyme complex from bovine seminal vesicles and human platelets are similar. The enzymes from the two tissues have similar kinetic properties and pH dependence, as well as ability to bind unsaturated fatty acid precursors. In addition, the I$_{50}$ values for aspirin and indomethacin do not differ significantly between the two enzyme sources.

With the findings that the aza-analogs apparently do not block the cyclooxygenase enzyme, attention was given to the possibility that these compounds act by inhibiting thromboxane synthesis or by blockade of the thromboxane and/or endoperoxide receptor(s). It has been shown that the formation of thromboxanes is closely associated with the initiation of platelet aggregation and occurs rapidly (within 30 sec.) when induced by arachidonic acid. Therefore, the aggregating effect of thromboxane A$_2$ can be studied by first generating the agent in one sample of PRP, and then transferring a portion of this to a second sample of PRP. In order to eliminate the possibility that aggregation is due to transferred arachidonic acid, the second sample of PRP is pretreated with aspirin at a concentration that totally inhibits cyclooxygenase activity. Thus, any aggregation induced by transferred material is due to thromboxane A$_2$ and/or prostaglandin endoperoxides. Using this protocol, it was found that aspirin-treated platelets were irreversibly aggregated when induced by the transferred, arachidonate-treated platelet suspension. However, when the aspirin-treated platelets were preincubated with 100 $\mu$M trans-13-azaprostanoic acid, aggregation induced by the transferred thromboxane A$_2$/endoperoxide mixture was totally inhibited. This experiment was repeated several times with identical results.

The effect of 13-APA on TXA$_2$ synthesis was assessed by measuring platelet conversion of AA to thromboxane B$_2$ (TXB$_2$), the inactive stable metabolite of TXA$_2$. Platelet rich plasma was aggregated with 500 $\mu$M arachidonic acid and three minutes following arachidonate addition, aliquots of the plasma were drawn for TXB$_2$ determinations. TXB$_2$ formation was measured by radioimmunoassay and is reported in Table IV.

TABLE IV

| Substance | TXB$_2$ (ng/ml) | % Aggregation |
|---|---|---|
| Arachidonic Acid (AA) (500 $\mu$M) | 1179 ± 37 | 80 |
| AA + Indomethacin (20 $\mu$M) | 13 ± 2 | 0 |
| AA + Imidazole (200 $\mu$g/ml) | 138 ± 8 | 5 |
| AA + Imidazole (100 $\mu$g/ml) | 264 ± 7 | 11 |
| AA + Imidazole (20 $\mu$g/ml) | 669 ± 33 | 21 |
| AA + 13-APA (50 $\mu$M) | 750 ± 19 | 0 |
| AA + 13-APA (10 $\mu$M) | 1164 ± 25 | 80 |

It can be seen that inhibition of cyclooxygenase activity by 20 $\mu$M indomethacin almost completely blocks platelet TXB$_2$ production. Similarly, a high concentration of imidazole (200 $\mu$g/ml), also results in a substantial depression of TXB$_2$ formation. As the concentration of imidazole is decreased from 200 $\mu$g/ml to 20 $\mu$g/ml TXB$_2$ levels rise but still remain significantly lower than control. In each case the extent of platelet aggregation is in accordance with the relative amounts of TXB$_2$ produced. Indomethacin totally blocks aggregation, whereas, 20 $\mu$g/ml imidazole inhibits aggregation approximately 75%. In contrast 13-APA (50 $\mu$M) completely inhibits aggregation, but only decreases TXB$_2$ formation by 36%. Such a decrease in thromboxane synthesis could certainly not account for the inhibitory properties of the compound. Rather, the observed fall in TXB$_2$ production with 13-APA probably reflects direct inhibition of secretion as opposed to inhibition of thromboxane synthetase activity. Thus, platelet production of TXA$_2$ from externally added arachidonate results in the secretion of granular ADP, which in turn recruits the further generation of TXA$_2$ from endogenous stores of arachidonate. Direct antagonism of TXA$_2$ stimulated secretion by 13-APA could therefore block the component of TXA$_2$ synthesis attributable to this regenerative process. As a result, TXB$_2$ formation would be reduced even in the face of intact thromboxane synthetase activity.

This possibility was examined by measuring the effect of 13-APA on TXB$_2$ formation in response to added PGH$_2$ (0.13 $\mu$g/ml). Platelets were isolated from EDTA-treated (7.5 $\mu$M) PRP by centrifugation at 800 xg for 15 minutes. The platelet pellet was resuspended by gentle swirling in calcium-free Tyrode buffer (pH 7.4). Indomethacin (20 $\mu$M) was supplemented to the platelet suspension in order to block cyclooxygenase activity and, hence, conversion of endogenous AA to TXB$_2$. The results, shown in Table V, demonstrate that, whereas imidazole blocks thromboxane synthetase in a dose dependent manner, 13-APA even at 100 $\mu$M has no effect on platelet production of TXB$_2$. Furthermore, the lowest concentration of 13-APA employed i.e., 10 $\mu$M, is completely effective in inhibiting PGH$_2$-induced aggregation. Thus, a concentration of 13-APA one order of magnitude greater than that necessary to totally block aggregation does not inhibit thromboxane synthetase activity. These results clearly establish that 13-APA inhibits AA-induced aggregation subsequent to the synthesis of $TXA_2$. Moreover, if it is assumed that $TXA_2$ is the final mediator involved in prostaglandin activation, 13-APA must act to block the interaction of $TXA_2$ with the platelet receptor.

TABLE V

| Substance | $TXB_2$ (ng/ml) | % Aggregation |
|---|---|---|
| $PGH_2$ (0.13 μg/ml) | 37 ± 3 | 30 |
| $PGH_2$ + Imidazole (200 μg/ml) | 3 ± 1 | 60 |
| $PGH_2$ + Imidazole (100 μg/ml) | 6 ± 1 | 50 |
| $PGH_2$ + Imidazole (20 μg/ml) | 26 ± 1 | 30 |
| $PGH_2$ + 13-APA (100 μM) | 40 ± 2 | 0 |
| $PGH_2$ + 13-APA (50 μM) | 44 ± 2 | 0 |
| $PGH_2$ + 13-APA (10 μM) | 50 ± 2 | 0 |

Additional evidence that 13-APA interferes with platelet activation at the receptor level was obtained using the direct agonist (15S)-hydroxy-9α,11α-(epoxymethano) prosta-5z, 13E dienoic acid (9-epoxy CEE). It was found that aggregation induced 3 μM 9-epoxy CEE is completely inhibited by 100 μM 13-APA and inhibited approximately 60% by 10 μM 13-APA. This finding further demonstrates that 13-APA is effective in antagonizing direct stimulation of the platelet receptor. Such inhibitory activity has not been previously reported for any compound which selectively blocks AA-induced aggregation.

The above assays examine the mechanism by which compounds of the invention inhibit blood platelet aggregatory functions and are believed to demonstrate that they are selective and potent antagonists of arachidonic acid-induced aggregation. Their inhibitory properties are essentially limited to the prostaglandin-stimulated platelet reaction, since they in no way alter primary aggregation in response to ADP or thrombin. Moreover, the results establish that they inhibit neither cyclooxygenase nor thromboxane synthetase activity but are capable of completely inhibiting aggregation in the face of elevated $TXA_2$ levels. The specifity of the compounds in antagonizing the action of $TXA_2$ is particularly striking when it is considered that $TXA_2$ formation from $PGH_2$ is not blocked by a ten-fold greater concentration of the compounds than that which totally inhibits aggregation.

Thus, the compounds of the present invention, when administered in effective amounts, are demonstrably active in the antagonism of activity of prostaglandin $H_2$ and thromboxane $A_2$ within the circulatory system.

Numerous modifications and variations of the above disclosure of preferred embodiments of the invention are expected to occur to those skilled in the art and therefore only those limitations as appear in the appended claims should be placed thereon.

What is claimed is:

1. Azaprostanoic acids of the formula

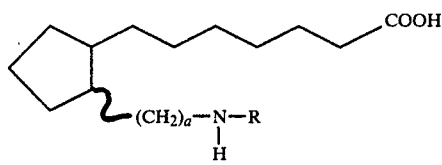

wherein: R is $C_1$ to $C_8$ alkyl or benzyl; and a has a value of from 0 to 6 inclusive, and their pharmaceutically acceptable salts and lower alkyl esters.

2. Compounds according to claim 1 wherein the sum of the numerical value of a and the number of carbon atoms in the R group totals 7.

3. Azaprostanoic acids according to claim 1 wherein a has a value of 0.

4. Azaprostanoic acids according to claim 1 wherein a has a value of 2.

5. A compound according to claim 1 which is named, 13-azaprostanoic acid, and its pharmaceutically acceptable salts and esters.

6. A compound according to claim 1 which is named, 15-azaprostanoic acid, and its pharmaceutically acceptable salts and esters.

7. The method of antagonizing the activity of prostaglandin $H_2$ and thromboxane $A_2$ in the circulatory system of an animal, said method comprising administering to the circulatory system of the animal an effective amount of an azaprostanoic acid of the formula,

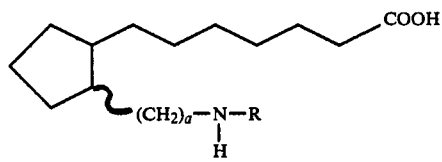

wherein: R is $C_1$ to $C_8$ alkyl or benzyl; and a has a value of from 0 to 6 inclusive, or its pharmaceutically acceptable salts and lower alkyl esters.

8. The method of claim 7 wherein the amount of azaprostanoic acid administered comprises from about 1 to about 100 mg/kg.

9. A pharmaceutical composition suitable for use in antiplatelet therapy, said composition comprising, as an active ingredient, an azaprostanoic acid compound of the formula

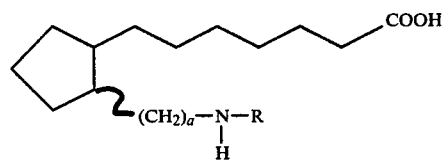

wherein: R is $C_1$ to $C_8$ alkyl or benzyl; and a has a value of from 0 to 6 inclusive, or its pharmaceutically acceptable salts and lower alkyl esters, in combination with a pharmaceutically acceptable carrier for said active ingredient.

* * * * *